(12) United States Patent
Braun (10) Patent No.: US 7,674,255 B2
(45) Date of Patent: Mar. 9, 2010

(54) SURGICAL INSTRUMENT (75) Inventor: Marcus Braun, Stuttgart-Vaihingen (DE)

(73) Assignee: Tuebingen Scientific Surgical Products, GmbH, Tuebingen (DE)

(*) Notice: Subject to any disclaimer, the term of this patent is extended or adjusted under 35 U.S.C. 154(b) by 887 days.

(21) Appl. No.: 10/815,395

(22) Filed: Apr. 1, 2004

(65) Prior Publication Data
US 2004/0260335 A1 Dec. 23, 2004

(30) Foreign Application Priority Data
Apr. 1, 2003 (DE) ................. 103 14 828
Apr. 1, 2003 (DE) ................. 103 30 604

(51) Int. Cl.
A61B 17/00 (2006.01)
(52) U.S. Cl. .......................... 606/1; 606/205
(58) Field of Classification Search ............... 606/1, 606/51–52, 205–208
See application file for complete search history.

(56) References Cited

U.S. PATENT DOCUMENTS

| | | | | |
|---|---|---|---|---|
| 5,147,357 A | * | 9/1992 | Rose et al. | 606/49 |
| 5,174,300 A | * | 12/1992 | Bales et al. | 600/564 |
| 5,275,608 A | * | 1/1994 | Forman et al. | 606/170 |
| 5,318,589 A | * | 6/1994 | Lichtman | 606/205 |
| 5,330,502 A | * | 7/1994 | Hassler et al. | 606/205 |
| 5,350,391 A | * | 9/1994 | Iacovelli | 606/170 |
| 5,374,277 A | * | 12/1994 | Hassler | 606/207 |
| 5,472,451 A | * | 12/1995 | Freitas et al. | 606/205 |
| 5,474,571 A | * | 12/1995 | Lang | 606/205 |
| 5,545,148 A | * | 8/1996 | Wurster | 604/223 |
| 5,549,637 A | * | 8/1996 | Crainich | 606/207 |
| 5,582,617 A | * | 12/1996 | Klieman et al. | 606/170 |
| 5,603,723 A | * | 2/1997 | Aranyi et al. | 606/205 |
| 5,607,450 A | * | 3/1997 | Zvenyatsky et al. | 606/206 |
| 5,609,601 A | * | 3/1997 | Kolesa et al. | 606/170 |
| 5,643,294 A | * | 7/1997 | Tovey et al. | 606/148 |
| 5,702,408 A | * | 12/1997 | Wales et al. | 606/139 |
| 5,743,456 A | * | 4/1998 | Jones et al. | 227/176.1 |

(Continued)

FOREIGN PATENT DOCUMENTS

DE 43 04 353 A1 4/1994

(Continued)

OTHER PUBLICATIONS

Scientific Article written by A. Melzer, M. Schurr, P. Dautzenberg, R. Trapp and G. Bueβ, entitled: "Increasing the Degrees of Freedom of Instruments in Minimally Invasive Surgery," 1992. See Summary in English on sixth page.

Primary Examiner—Michael Peffley
Assistant Examiner—Alex Toy
(74) Attorney, Agent, or Firm—Hanley, Flight & Zimmerman, LLC (57) ABSTRACT A surgical instrument comprising an instrument handle linked to a proximal end portion of a tube shaft to the distal end portion of which an instrument head is linked so as to be inclinable, in which instrument head, in turn, an effector including at least one pivotable engaging element is rotatably supported. The instrument handle comprises a number of manipulators and/or operating mechanisms designed for operating the instrument head and/or the effector. One of the manipulators consists of an operating element in the form of a rotary knob with respect to its function, the operating element being rotatably supported on the instrument handle.

17 Claims, 5 Drawing Sheets

U.S. PATENT DOCUMENTS

| | | | |
|---|---|---|---|
| 5,797,958 A * | 8/1998 | Yoon | 606/207 |
| 5,827,323 A * | 10/1998 | Klieman et al. | 606/205 |
| 5,868,785 A | 2/1999 | Tal et al. | |
| 5,954,731 A * | 9/1999 | Yoon | 606/144 |
| 5,976,121 A | 11/1999 | Matern et al. | |
| 5,993,467 A | 11/1999 | Yoon | |
| 5,997,565 A * | 12/1999 | Inoue | 606/205 |
| 6,068,647 A * | 5/2000 | Witt et al. | 606/205 |
| 6,540,737 B2 | 4/2003 | Bacher et al. | |
| 6,666,854 B1 * | 12/2003 | Lange | 606/1 |
| 6,889,116 B2 * | 5/2005 | Jinno | 700/245 |
| 6,936,061 B2 * | 8/2005 | Sasaki | 606/205 |
| 2002/0055758 A1 * | 5/2002 | Sasaki | 606/205 |

FOREIGN PATENT DOCUMENTS

| | | |
|---|---|---|
| DE | 100 36 108 A1 | 11/2001 |
| NL | 1004375 C | 5/1998 |

* cited by examiner

SURGICAL INSTRUMENT

BACKGROUND OF THE INVENTION

1. Field of the Invention

The present invention relates to a surgical instrument for minimally invasive surgery.

2. Discussion of the Prior Art

From DE 100 36 108, a surgical instrument of this generic type is known. It substantially consists of a tube shaft at the one proximal end of which an instrument handle is arranged for the operation of an instrument head disposed at the opposed distal end of the tube shaft via gear trains. The instrument head can be bent, or rather inclined, with respect to the tube shaft and, moreover, holds an effector rotatably supported in the instrument head in the form of a type of forceps or tongs one jaw of which is pivotably supported on the effector and is likewise operable by means of the instrument handle.

In more concrete terms, the gear trains enable at least a first movement of the instrument handle, according to this prior art to be triggered by rotation of an operator's hand, to be transformed into a rotation of the effector at a predetermined transmission ratio with respect to this operating movement. This makes it possible to rotate the effector despite the relatively restricted possibility of motion of a human hand about up to 300°, for instance, and, thus, to realize complex motions without changing the grip at the handle. Moreover, a second movement of the instrument handle, for instance bending the same with respect to the tube shaft, is converted into an inclination movement of the instrument head.

The gear trains provided inside the instrument handle and the tube shaft are designed such that a most largely decoupled operation of each individual movement of the instrument head and the effector is permitted. However, such gears are necessarily extremely complex and consequently also require sufficient assembly space. Moreover a complete decoupling of the individual movements is not completely ensured.

It has also turned out that, especially in the case of a hand rotation for turning the effector supported in the instrument head, the natural structure of the hand and the motions resulting therefrom, i.e. irrespective of whether or not the gear trains of the surgical instrument are in fact completely decoupled, at the same time cause a slight bending of the instrument head and, moreover, a tilting (staggering) of the entire instrument shaft, which considerably impedes the handling of the instrument.

In view of this prior art, it is the object of the present invention to provide a surgical instrument of this generic type in which motions of an instrument head as well as of an effector can be performed, largely independently of the natural conditions of a natural hand structure, decoupled from each other via an instrument handle.

SUMMARY OF THE INVENTION

This object is achieved by a surgical instrument comprising an instrument handle linked to a proximal end portion of a tube shaft, the tube shaft having a distal end portion linked to an instrument head, so as to allow the instrument head to bend relative to the tube shaft. The instrument head further comprises a rotatably supported effector having at least one pivotable element. The handle has a plurality of manipulators and/or operating mechanisms for operating the instrument head and/or the effector, wherein a first manipulator further comprises an operating element having the shape of a rotary knob and is rotatably supported on the instrument handle.

In principle, the basis of the invention is formed by an exact knowledge of individual motion patterns of a human hand on the basis of which then functions can be advantageously allocated to the individual manipulators at an instrument handle. Herefrom, constructional measures for the manipulators themselves can be taken for the ergonomic adaptation thereof to the human hand. To put it more concretely, especially the fingers of a human hand are equipped with a precision motoricity which is adapted to precisely carry out even minimal movements without other motion processes having to take place at the hand, or rather have to assist the same.

On the basis of this, the core of the invention now consists in providing the instrument handle with an operating knob rotatably supported with respect to the handle member or with an operating element assuming the function of such a knob as a manipulator to perform a rotation of the effector.

This operating knob or element thus can be rotated by means of selected fingers (preferably thumb and index), while the handle member is held fast in the hand. The rotation is effected completely separately from other motion processes of a human hand, i.e. it is not superimposed by turning or bending a wrist joint. Moreover, the operating knob conveys a distinct tactile feeling to a surgeon, which considerably improves the handling of the instrument.

It is advantageous to arrange the rotary knob at a free front face end of the handle member, whereas the handle member itself is linked to the instrument shaft at its other, rear end pivotably as well as laterally offset with respect to the instrument shaft. Ideally, the link between the handle member and the instrument shaft should coincide with the wrist joint of an operator. Constructively, this is possible only approximately by selecting the length of the handle member and/or the distance between the link and the handle member portion gripped by the operator's hand to be such that the link is arranged as exactly as possible below the wrist joint, i.e. as closely as possible to the wrist joint. Thus, a bending motion at the wrist of a human hand is transferred to the handle member without causing, in turn, a rotational movement of the operating knob or a staggering of the instrument shaft. The turning of the operating knob by an appropriate movement of the fingers may then again be effected individually in any bending position of the wrist joint. The bending movement of the handle member advantageously leads to a bending of the instrument head with respect to the instrument shaft.

It is further advantageous to arrange a pivoting lever, similar to a bicycle brake lever, on the handle member in such a way that it is operable by means of the fingers or one of the still remaining fingers without the handle member having to be let loose. Preferably, the pivoted lever is linked to a lower side of the handle member and is urged against the handle member by at least one finger. This pivoting movement of the pivoted lever preferably results in an operation of the effector, or rather in triggering the function of the effector.

Further advantageous configurations of the invention are the subject matter of the dependent claims.

BRIEF DESCRIPTION OF THE DRAWINGS

Hereinafter, the invention will be explained in detail by example of a preferred embodiment with reference to the accompanying drawings, in which.

DETAILED DESCRIPTION OF THE PREFERRED EMBODIMENTS

Figure 1:
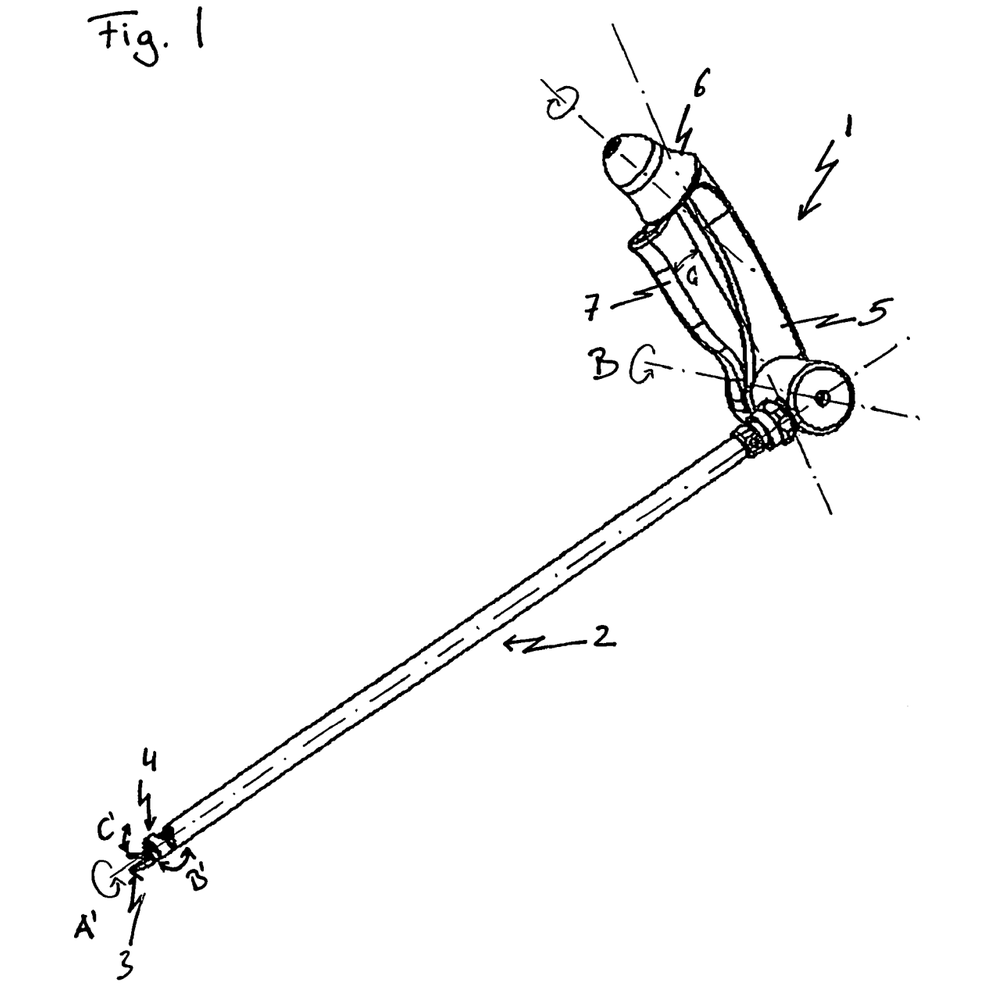
FIG. 1 shows a perspective view of a surgical instrument according to a preferred embodiment of the invention.

In FIG. 1, a complete surgical instrument according to a preferred embodiment of the invention is shown in a perspective view. The surgical instrument according to the invention consequently has a multi-functional instrument handle 1 which is arranged at a proximal end or end portion of a tube shaft 2, preferably made of stainless steel, a steel alloy or a synthetic material, as well as an instrument head 4 equipped or adapted to be equipped with an effector 3, the instrument head being provided at the other, distal end of the tube shaft 2.

In general, the instrument head 4 is supported at the respective tube shaft end such that it can be pivoted or bent with respect to the tube shaft 2, whereas the effector 3 can be turned or rotated in each bending position of the instrument head 4 about the longitudinal axis of the latter, the two aforementioned motions being adapted to be performed by means of the instrument handle 1. To this end, a number of manipulators or operating mechanisms are provided at the instrument handle 1 and are operatively connected, via corresponding gear trains inside the instrument handle 1 as well as inside the tube shaft 2, to the instrument head 4 and the effector 3, respectively, so as to be able to perform the individual motions of the instrument head 4 and of the effector 3 independently of each other, i.e. in a decoupled manner.

Specifically, the instrument handle 1 consists of an ergonomically shaped handle piece 5 which is mounted in a pivotable and inclinable manner to the tube shaft 2 and on which a first manipulator 6, in the present case preferably in the form of a rotary knob, and a second manipulator 7, in the present case preferably in the form of a handle lever, are supported. Thus, the instrument handle 1 according to the preferred embodiment of the present invention comprises a total of three operating mechanisms for three independent movements of the effector 3 and/or the instrument head 4. It is explicitly emphasized in this context that the instrument handle 1 may also have fewer operation possibilities, for instance only one manipulator or operating mechanism, respectively, for pivoting the instrument head 4 and rotating the effector 3.

Figure 2:
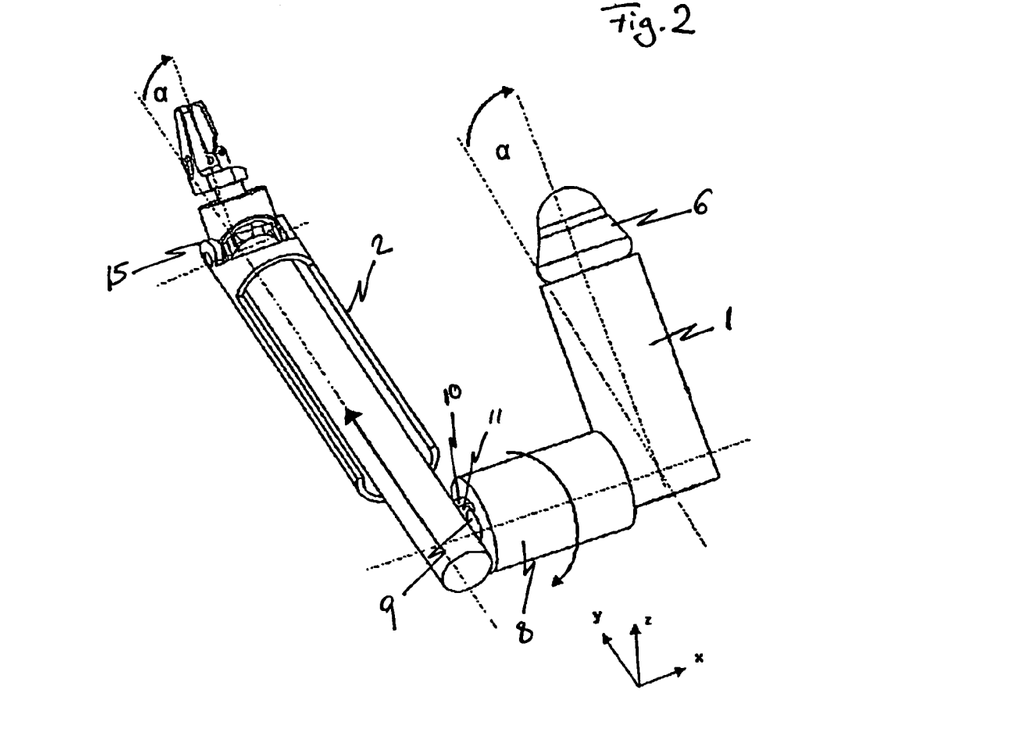
FIG. 2 shows a first gear train for pivoting an instrument head by means of an instrument handle.
Figure 3:
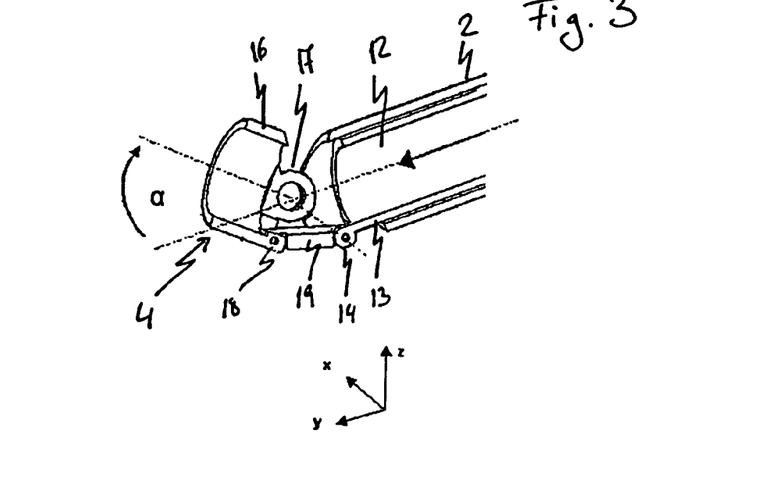
FIG. 3 shows a partial section of the first gear train in the pivoting range of the instrument head.

The exterior structure of the instrument handle 1, especially with respect to the operating mechanism for pivoting and bending the instrument head 4 and with respect to the corresponding bending gear train is shown in FIGS. 2 and 3.

The handle 1 schematically shown in FIG. 2 is pivotably connected to the tube shaft 2 via a crank member 8 which is fixedly connected to the handle member 5 and has the form of a rotary shaft or rotary disk. The rotary shaft 8 is preferably aligned so as to be perpendicular to the tube shaft 2 as well as to the handle member 5 and spaces the handle member 5 from the tube shaft 2 such that the handle 1 can be pivoted substantially in parallel to the tube shaft past the same.

The rotary shaft 8, forming a central through passage 9 for accommodating the gear members described hereinafter, is shaped at its one front face facing the tube shaft 2 to have a crank guide 10 in the form of a cam-shaped groove in which a driving pin 11 engages which is attached to an axially shiftable pushing tube 12 supported in the tube shaft 2. The groove 10 is formed such that, during a rotation of the rotary shaft 8, the driving pin 11 slides along in the groove 10 by an appropriate pivoting of the handle member 5 and, in so doing, performs a forced compensating motion in the longitudinal direction of the tube shaft 2, said motion being transmitted to the pushing tube 12 and resulting in a reciprocating motion of the pushing tube 12 inside the tube shaft 2 depending on the direction of rotation of the rotary shaft 8.

The distal end portion of the pushing tube 12 opposite to the crank member 8 is formed so as to have a longitudinally extending mounting link 13 which projects from the distal end of the pushing tube 12 and forms a hinge or hinge eyes 14 at its free end portion. Moreover, the front face of the tube shaft 2 is chamfered at its distal end portion at an angle of preferably 45° and includes lateral link eyes 15 at which the instrument head 4 is pivotably linked via link joints or pins. The instrument head equally consists of a tube member 16 at whose end control eyes 17 for connection to the tube shaft 2, or rather to the link eyes 15 thereof, are formed is likewise chamfered at an angle of preferably 45°, namely in such manner that, after linking the instrument head 4 to the tube shaft 2, the two aforementioned chamfers complement each other and enable the tube member 16 to be bent with respect to the tube shaft 2 by approximately 90°, preferably 70°.

Moreover, a hinge, or rather hinge eyes 18, are formed at the chamfered end of the tube member 16. To each tile hinge eyes 14; 18 provided at the pushing tube side the tube member side, a rocking lever 19 is hinged, is consequently offset radially outwardly with respect to the pivot axis of the instrument head 4 and transmits an axial translation movement of the pushing tube 12 to the tube member 16 whereby the latter is pivoted about its own pivot axis.

Hereinafter, the operating mechanism for a rotation of the effector 3 supported in the instrument head 4 and the corresponding rotation gear train are described by way of FIG. 4 and FIG. 5.

As can further be taken from FIG. 2, the aforementioned tube member 16 of the instrument head 4 at the same time constitutes a housing and/or a receptacle for the effector 3. Independently of the type of effector, i.e. independently of whether, for instance, a needle holder, tongs, forceps or scissors are used as effector, the latter has a preferably hollow rotational shaft 20 which is rotatably inserted in the tube member 16 of the instrument head 4 and is secured against an axial movement. The length of this rotational shaft is selected such that it ends approximately in the area of the pivot shaft of the instrument head 4 and is provided at its free end projecting toward this pivot axis with an output spur gear 21 which is attached to the rotational shaft 20 of the effector 3 in a torque-proof manner. Especially in FIG. 2, the pivot axis of the instrument head 4 is shown by a broken line through the eyes 15.

Figure 4:
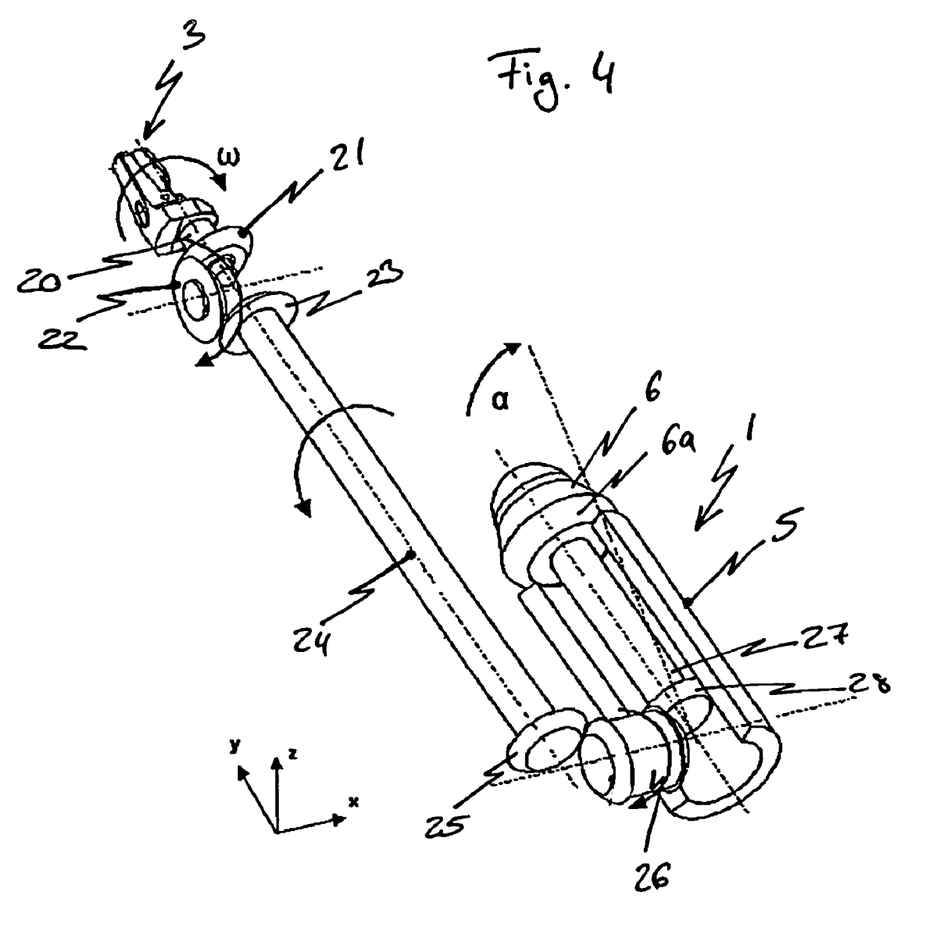
FIG. 4 shows a second gear train for rotation of the instrument head by means of the instrument handle.
Figure 5:
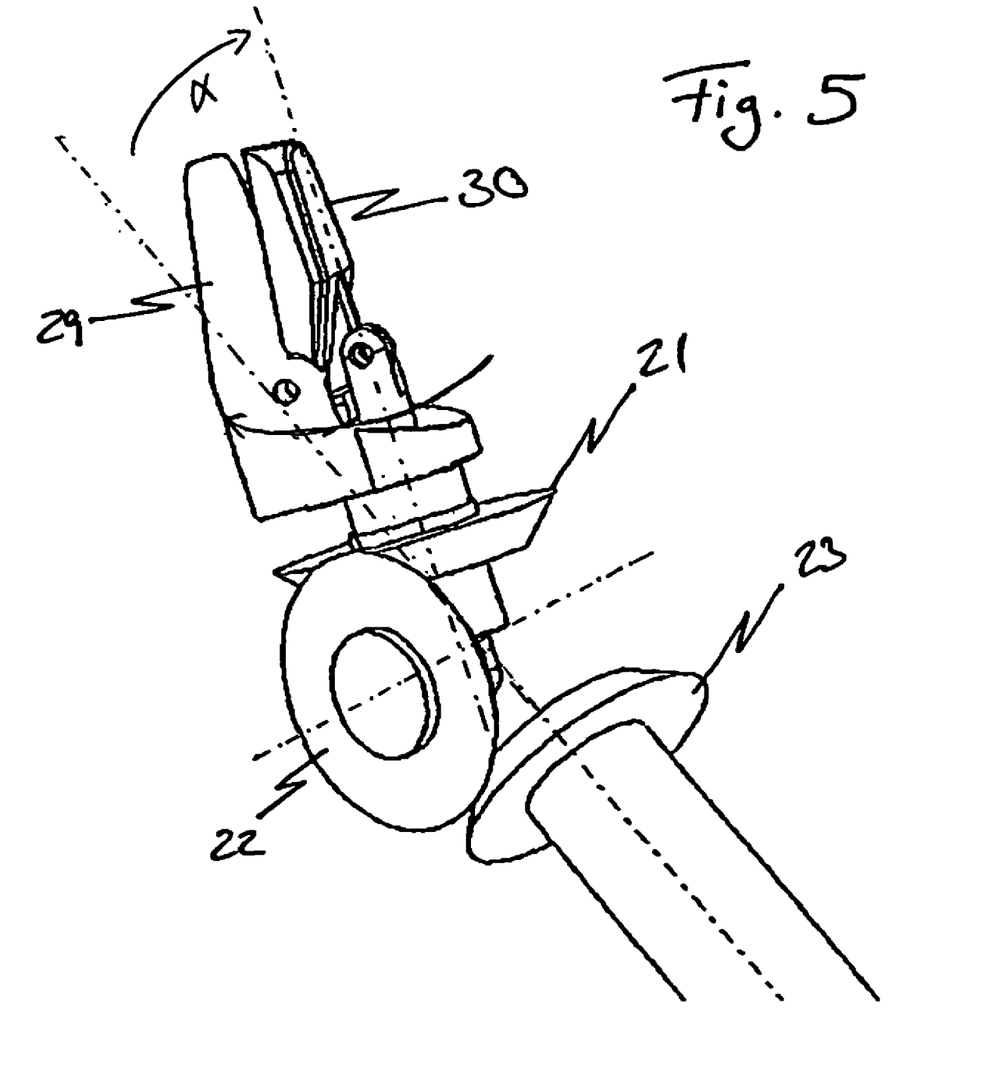
FIG. 5 shows a partial section of the second gear train in the pivoting range of the instrument head.

As can further be taken from FIG. 5, on the pivot axis of the instrument head 4, a torque transmission spur gear 22 is provided; it is rotatably supported on one of the two pivot pins of the two pivot pins of the instrument head 4, not shown in detail, which form the schematically shown pivot axis, and is in mesh with the output spur gear 21. The torque transmission spur gear 22 in its turn is in mesh with a drive spur gear 23 which is fixedly mounted on a drive shaft 24 rotatably guided inside the pushing tube 12 (not shown in FIGS. 4 and 5), as this is especially shown in FIG. 4. According to FIG. 4, another torque initiating spur gear 25 is arranged in a torque-proof manner at one end of the drive shaft 24 opposed to the drive spur gear 23 and is in mesh with a long-face pinion 26 supported in the central through passage 9 formed inside the crank member 8. The crank member 8 is not shown in detail in FIG. 4.

Finally, the long-face pinion 26 is in mesh with an actuating shaft 27, or rather with a spur gear 28 fastened thereto inside the handle 1, said shaft being fixedly connected to the one manipulator, the rotary knob 6 in the present case.

As can be seen especially from FIG. 4, the rotary knob 6 forms the distal tip or the outer end of the instrument handle 1. It is fixedly connected to the actuating shaft 27 extending substantially along the longitudinal axis of the handle member 5. In this context, it is referred to the fact, however, that the rotary knob 6, or rather the axis of rotation thereof, may also be advantageously inclined downwards and/or laterally with respect to the actuating shaft 27, preferably by approximately 18° to 25°, for which purpose the actuating shaft 27 may be provided with a universal joint or a cardan mechanism not shown in detail. Such an angular position of the rotary knob 6 or of a corresponding rotary element further improves the ergonomics of the instrument handle 1.

The rotary knob 6 includes a rear edge portion 6a facing the handle member 5 which is schematically shown as a sleeve in FIG. 4, said edge portion being opposed to the handle member 5 while forming a gap of a relatively large gap dimension and, thus, leaves the handle member 5 open at its distal end via the gap. Any dirt in the gear section located in the handle member can, thus, be easily removed without dismounting the handle.

When the rotary knob 6 is operated, the rotation thereof is transmitted via the actuating shaft 27 inside the handle 1, the long-face pinion 26, the subsequent drive shaft 24 inside the pushing tube 12 as well as the transmission spur gear 22 to the effector 3, and the latter is turned. The rotary knob 6 is advantageously operated by the fingers, especially by the thumb and the index of the operator's hand while the handle member 5 is held in the hand. Thus, it is possible to generate any rotation at the effector 3 without the operator having to change his grip at the handle member 5 itself. The fingers of a human hand are able to work in a fine-motor way and also the finger tips are provided with a plurality of nerve ends permitting a distinct tactile feeling. Accordingly, movements requiring high accuracy should be performed by the fingers. It has turned out that the rotation of the effector 3 is such a movement and is, therefore, triggered by the rotary knob 6 according to the invention without a movement being advantageously transmitted to the tube shaft 2 by the rotary knob 6 for a rotation of the effector 3. Rather, an operator's hand can be maintained steady.

In this context, it is further referred to the fact that the drive shaft 24 and the pushing tube 12 are supported in the axial direction to be relatively movable with respect to each other, i.e., a rotation of the crank member 8 triggered by pivoting the instrument handle 1 does cause a translation movement of the pushing tube 12. Yet, at the same time, the drive shaft 24 is held in position, i.e. in mesh with the long-face pinion 26, whereby the pushing tube 12 performs an axial relative movement with respect to the tube shaft 2 and to the drive shaft 24.

Ultimately, hereinafter the operating mechanism for the effector 3, i.e. the functions thereof, and for the corresponding effector gear train is described by reference to FIGS. 5 and 6a-6c.

According to FIG. 5, in the present embodiment of the invention, the effector 3 is designed as tongs including a fixed jaw and a movable, i.e. pivotable jaw 29; 30. The fixed jaw 29 forms a unit together with the rotating shaft 20 and is preferably formed integrally with the rotating shaft 20, whereas the movable jaw 30 is linked to the fixed jaw 29 at one end.

The movable jaw 30 forms a linking point 31 for a pushing pin 32 which is supported inside the rotating shaft 20 so as to be relatively shiftable, so that a pivoting movement of the movable jaw 30 with the maximum possible transmission is caused by the axial shifting of the pushing pin. As this is especially shown in FIGS. 6a-6c, the pushing pin 32 is biased by a spring 33 axially in the opening direction of the tongs enclosing the pushing pin 32 inside the rotating shaft 20. For this purpose, the pushing pin 32 has a shaft protrusion at which the biasing spring 33 is supported by its one end. The other end of the biasing spring 33 is supported against the fixed jaw 29. An end piece 34 of the pushing pin 32 projecting from the rotating shaft 20 towards the pivot axis of the instrument head 4 is formed as a ball-shaped head, the radius of the ball-shaped head 34 preferably being approximately 2.5 mm in the present case.

The aforementioned drive shaft 24 for rotating the effector 3 supported in the instrument head 4 is provided with a substantially continuous axial bore (not shown in detail). In this axial bore, a pushing rod 35 is guided to be axially shiftable as well as rotatably guided relative to the drive shaft 24, the front face of the pushing rod facing the pushing pin 32 being chamfered corresponding to the chamfers of the distal front faces provided at the tube shaft side and the pushing tube side, i.e. preferably 45° in the same direction. The pushing pin 32 is biased against this chamfered front face of the pushing rod 35 by the spring 33 and abuts against the same. The contact between the pushing rod 35 and the pushing pin 32 is substantially punctiform due to the afore-described ball-shaped head of the pin 32, namely independently of the degree of bending of the instrument head 4 and independently of the position of rotation of the effector 3.

Figures 6A, 6B:
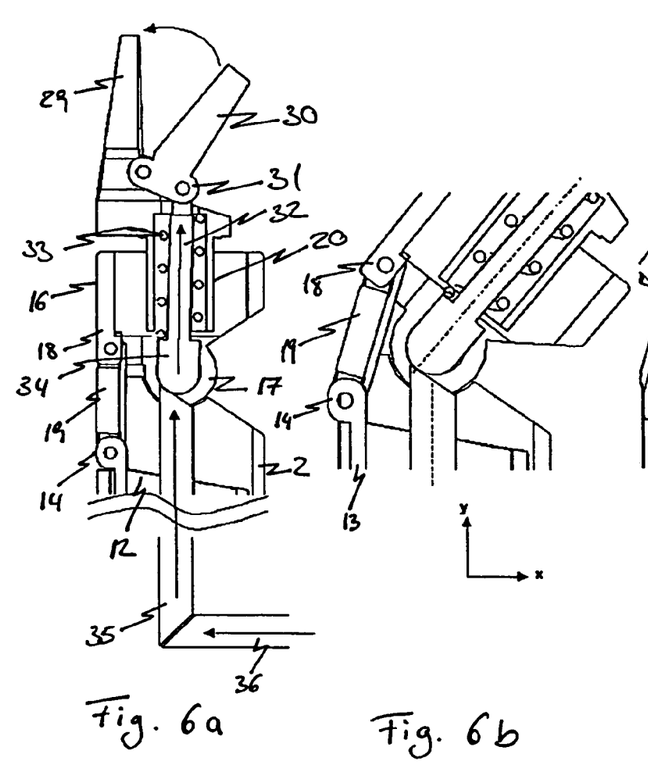
FIGS. 6a-6c show sectional views of a third gear train in the pivoting range of the instrument head for the operation of forceps supported at the instrument head.

As can be seen from FIG. 6a, the pushing pin 32 as well as the pushing rod 35 are aligned axially with respect to each other in case that the bending of the instrument head 4 with respect to the tube shaft 2 is substantially 0°. Moreover, in this position of the instrument head 4, the pushing pin 32 is positioned such that the center of the ball head 34 of the pushing pin 32 is located approximately in the pivot axis of the instrument head 4.

At its proximal end, the pushing rod 35 is connected via a gear mechanism 36, not shown in detail, to the actuating lever 7 which is pivoted to the handle 1, as already briefly explained at the beginning of this description. It is emphasized in this context that the operation of the effector mechanism, i.e. for instance opening and closing the tongs, need not always be a dynamic process, but that, quite often, the effector also has to be kept in a particular position. For this purpose, in the handle member, an arresting means which can be individually activated, for instance a spring-biased stop bolt or similar stop member, may be provided for interacting with the actuating lever 7 and optionally keeping the same in a position. It has turned out to be especially advantageous in this case to cause the triggering, or rather releasing, of such arresting means by way of the turning knob which, to this end, is supported to be longitudinally shiftable along its axis of rotation, for example, and which actuates the triggering, or rather releasing mechanism of the arresting means upon a shifting movement.

The aforementioned function is purely optional, however, so that it is not shown any further in the enclosed Figures. The essential operational modes of the surgical instrument according to the invention will, however, be described hereinafter in detail by way of the enclosed Figures.

A rotation of the effector 3 supported in the instrument head 4 is effected by an operation of the rotary knob 6 supported at one end of the handle 1, the rotary knob 6 being adapted to be turned about its axis of rotation, as already described in the foregoing, so far that a rotation of approximately 360° is realized for the effector 3 without the necessity to change the grip at the handle member 5. This rotation is transmitted via the actuating shaft 27 to the long-face pinion 26 which, in its turn, transmits its rotation to the drive shaft 24 extending inside the pushing tube 12. The rotation of the drive shaft 24 causes a rotation of the transmission spur gear 22 which quasi bridges the pivot axis of the instrument head 4 and, thus, triggers a motion of rotation of the effector 3 inside the tube member 16 of the instrument head 4 about the axis of the tube member.

According to the present embodiment, the entire handle 1 has to be pivoted about the longitudinal axis of the crank member 8 to effect a bending, i.e. a pivoting movement of the instrument head 4 and, thus, of the effector 3. In other words, a pivoting movement of the handle 1 with respect to the tube shaft 2 causes a rotation of the crank member 8 fixedly connected to the handle 1. At the same time, however, the long-face pinion 26 is rotated along with the crank member 8 due to the fact that a kind of automatic lock by friction (efficiency of the gear mechanism) occurs by the mesh between the actuating shaft 27 and the long-face pinion 26, said lock being possibly further assisted by slightly holding the operating knob 6 and by the static friction between the operating knob 6 and the handle member 5.

The rotation of the crank member 8 is transmitted via the crank or rather groove 10 at the end of the member 8 as well as the driving pin 11 into an axial movement of the pushing tube 12, which is transformed via the hinged rocking lever 19 into a pivoting movement of the instrument head 4 about the pivot axis thereof. However, this pivoting movement is automatically also performed by the output spur gear 21 which is fixed to the rotation axis of the effector 3 and is in mesh with the transmission spur gear 22. If, accordingly, the transmission spur gear 22 were stationary in this kind of operation, i.e. the pivoting operation, the pivoting movement of the instrument head 4 would cause the output spur gear 21 to roll off the transmission spur gear 22 in the same direction and, thus, would inevitably result in a superimposed rotation of the effector 3.

As described in the foregoing, however, the long-face pinion 26 is rotated along with the crank member 8 during a pivoting movement of the handle member 5 and, thus, drives the drive shaft 24 inside the pushing tube 12. The transmission between the long-face pinion 26 and the drive shaft 24 is calculated such that the transmission gear 22 is rotated by the drive shaft 24 about such an angle of rotation corresponding to the angle of rotation which is caused by the output gear 21 during a corresponding bending of the instrument head 4, whereby both rotations compensate each other due to their counter-rotation. In this configuration, the relative position between the transmission spur gear 22 and the output spur gear 21 is maintained even during the bending motion of the instrument head 4, so that the effector 3 is held in each bending position of the instrument head 4 as well as during a bending motion, in its current position of rotation with respect to the instrument head 4.

In order to bring about the operation of the effector 3, i.e. the function thereof itself, the lever 7 pivotably supported on the handle member 5 is provided in the present preferred embodiment. As already described in the foregoing concerning FIGS. 6a-6c, lever 7 is operatively connected, via a reversing gear not shown in detail or an appropriate joint mechanism, to the pushing rod 35 which is supported in the rotary shaft 24 and which axially reciprocates relative to the rotary shaft 24 upon a corresponding operation of the lever 7. A simple Bowden cable or deflecting lever would also be conceivable for power transmission to the pushing rod 35.

Figure 6C:
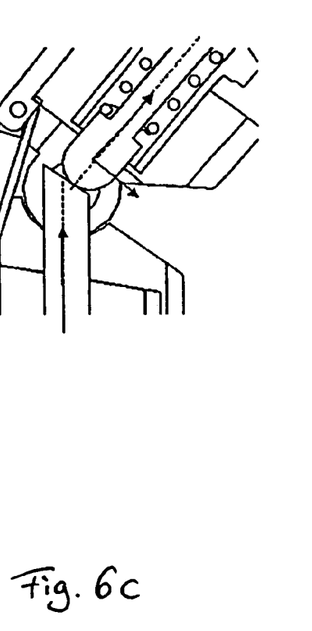

FIG. 6a shows the relative position of the pushing rod 35 and the pushing pin 32 in a bending position of the instrument head 4 of 0° with the tongs being opened, FIG. 6b shows the relative position of the pushing rod 35 and the pushing pin 32 in a bending position of the instrument head 4 of approximately 45° with the tongs being opened, and FIG. 6c shows the relative position of the pushing rod 35 and the pushing pin 32 in a bending position of the instrument head 4 of approximately 45° with the tongs being closed.

As can be seen from FIGS. 6a-6c, the pushing pin 32 is kept in constant contact with the beveled or chamfered distal front face of the pushing rod 35 by the biasing force of the spring 33. When the pushing rod 35 is shifted in the direction of the instrument head 4 in the case of a 0° bending of the instrument head 4 according to FIG. 6a, the pushing pin 32 is shifted at the same speed and over the same distance as the pushing rod 35, i.e. without transmission, against the biasing force of the spring 33, whereby the jaw 30 of the tongs linked thereto is pivoted in the closing direction.

In this context, it is referred to the fact that by the shifting action of the pushing rod 35, the pushing pin 32, i.e. especially the center of the pin head radius, remains only approximately on the pivot axis of the instrument head 4, i.e. it moves in a kind of circular orbit during a bending motion of the instrument head 4. As already explained at the beginning of the description of the figures, however, the regulating distances for opening and closing the tongs, for instance, are so small due to the transmissions set that, although the radius of the circular orbit can be calculated theoretically, it has no relevant influence on the position of the tongs for reasons of manufacture already (natural elasticity of the materials used, dimensional tolerances and play at the link joints and gear parts). In other words, the position of the tongs is determined by the position of the lever 7 which, in its turn, is held by an operator and, thus, is also subjected, for instance, to non-controllable movements of the hand (trembling motions). Such disturbances produced due to manual operations are greater by far and, therefore, practically solely relevant compared to those disturbances produced by the afore-described orbit motion.

That is to say, irrespective of the current position of the pushing rod 35 and the pushing pin 32, respectively, a bending of the instrument head 4 does generally not only cause the pushing pin 32 to pivot with respect to the pushing rod 35 but also causes the pin head 34 to slightly slide off the chamfered front face of the pushing rod 35. By this minor slide-off motion, the bearing contact of the pushing pin 32 with the front face is maintained, wherein only such a compensating longitudinal motion of the pushing pin 32 takes place as a result of its slide-off motion, however, which entails no practically relevant change of the closing or opening position at the effector 3. At the same time, however, a kind of power deflection mechanism is provided so as to bring about a longitudinal motion of the pushing rod 35 into a longitudinal motion of the pushing pin 32 now provided at an angular position with respect to the pushing rod 35 by the chamfering of the front face of the pushing rod.

In other words, if the pushing rod 35 is shifted in a bending position >0° according to FIG. 6b in the closing direction of the effector 3, as shown in FIG. 6c, the chamfered front face of the pushing rod 35 slides longitudinally past the pin head 34 while exerting an advance force on the pushing pin 32 which accordingly moves in the closing direction of the effector 3.

It should be understood that any of a variety of fastening means and suitable materials of construction and dimensions may be used to satisfy the particular needs and requirements of the end user. It also will be apparent to those skilled in the art that various modifications and variations can be made in the design and construction of a surgical instrument without departing from the scope or spirit of the invention.

I claim:

1. A surgical instrument comprising:
   an instrument handle having a front end and a rear end;
   a tube shaft having a proximal end portion and a distal end portion, wherein the proximal end portion is linked to the rear end of the instrument handle; and
   an instrument head, wherein the instrument head is linked to the distal end portion, so as to allow the instrument head to bend relative to the tube shaft, the instrument head further comprising a rotatably supported effector having at least one pivotable engaging element,
   wherein the instrument handle includes a plurality of manipulators and/or operating mechanisms for operating the instrument head and/or the effector, wherein a first manipulator further comprises an operating element having the shape of a rotary knob and being rotatably supported at the front end of the instrument handle, and wherein the instrument handle is pivotally supported at the tube shaft via a pivot shaft, such that the instrument handle including the first manipulator are aligned so as to be laterally offset with respect to the tube shaft.

2. A surgical instrument according to claim 1, wherein the instrument handle forms an operating mechanism for bending the instrument head with respect to the tube shaft.

3. A surgical instrument according to claim 2, wherein the instrument handle is constructively pivotable past a parallel position with respect to the tube shaft.

4. A surgical instrument according to claim 1, wherein the first manipulator in the shape of a rotary knob is rotatably arranged at a distal end portion of a handle member of the instrument handle and wherein the first manipulator is inclined with respect to the longitudinal axis of the instrument handle.

5. A surgical instrument according to claim 4, wherein the inclination of the rotary knob relative to the instrument handle is at an angle of approximately 20° to 25°.

6. A surgical instrument according to claim 2, wherein the first manipulator in the shape of a rotary knob is rotatably arranged at a distal end portion of a handle member of the instrument handle and wherein the first manipulator is inclined with respect to the longitudinal axis of the instrument handle.

7. A surgical instrument according to claim 1, wherein the first manipulator forms the distal tip of the instrument handle.

8. A surgical instrument according to claim 7, wherein the first manipulator is adapted to be operated by the fingers of a human hand.

9. A surgical instrument according to claim 1, wherein the first manipulator is operatively connected, via a gear train, to the effector.

10. A surgical instrument according to claim 9, wherein rotation of the first manipulator rotates the gear train which rotates the effector relative to the instrument head.

11. A surgical instrument according to claim 1, wherein a lever-shaped manipulator is arranged at a longitudinal side of the instrument handle and is pivotable relative to the instrument handle and operatively connected, via a gear train, to the effector.

12. A surgical instrument according to claim 11, wherein the lever-shaped manipulator is adapted to operate the effector.

13. A surgical instrument according to claim 1, wherein the instrument handle has an ergonomically shaped handle member on which the manipulators and/or operating mechanisms of the instrument handle are supported.

14. A surgical instrument comprising:
   an instrument handle having a front end and a rear end;
   a tube shaft having a proximal end portion and a distal end portion, wherein the proximal end portion is linked to the rear end of the instrument handle; and
   an instrument head, wherein the instrument head is linked to the distal end portion, so as to allow the instrument head to bend relative to the tube shaft, the instrument head further comprising a rotatably supported effector having at least one pivotable engaging element,
   wherein the instrument handle includes a plurality of manipulators and/or operating mechanisms for operating the instrument head and/or the effector, wherein a first manipulator configured to effect bending of the instrument head is formed between the front end of the instrument handle and the rear end of the instrument handle and further comprises a free end and a second manipulator further comprises an operating element having the shape of a rotary knob and being rotatably supported at the free end of the first manipulator of the instrument handle opposite to the linkage with the tube shaft, and wherein the instrument handle forms an operating mechanism for bending the instrument head with respect to the tube shaft.

15. A surgical instrument according to claim 1, wherein the first manipulator is adapted to be operated by the fingers of a human hand while the instrument handle is held fast in the hand.

16. A surgical instrument according to claim 1, wherein rotation of the instrument handle does not necessarily cause rotation of the first manipulator.

17. A surgical instrument comprising:
   a tube shaft having a first end and a second end;
   an instrument head coupled to the first end of the tube shaft; and
   an instrument handle coupled to the second end of the tub shaft, the instrument handle comprising:
      a first manipulator comprising an actuator shaft having a longitudinal axis; and
      a second manipulator coupled to the first manipulator along the longitudinal axis of the first manipulator, wherein the second manipulator comprises a rotary knob rotatable about the longitudinal axis of the first manipulator.

* * * * *